US011694884B2

(12) United States Patent
Wang

(10) Patent No.: US 11,694,884 B2
(45) Date of Patent: Jul. 4, 2023

(54) MASS SPECTRAL ANALYSIS OF LARGE MOLECULES

(71) Applicant: CERNO BIOSCIENCE LLC, Las Vegas, NV (US)

(72) Inventor: Yongdong Wang, Las Vegas, NV (US)

(73) Assignee: CERNO BIOSCIENCE LLC, Las Vegas, NV (US)

(*) Notice: Subject to any disclaimer, the term of this patent is extended or adjusted under 35 U.S.C. 154(b) by 15 days.

(21) Appl. No.: 17/108,835

(22) Filed: Dec. 1, 2020

(65) Prior Publication Data

US 2021/0104390 A1   Apr. 8, 2021

Related U.S. Application Data

(63) Continuation of application No. PCT/US2019/035173, filed on Jun. 3, 2019.

(Continued)

(51) Int. Cl.
*H01J 49/36* (2006.01)
*H01J 49/00* (2006.01)
*G01N 33/68* (2006.01)

(52) U.S. Cl.
CPC ...... *H01J 49/0036* (2013.01); *G01N 33/6848* (2013.01); *H01J 49/0009* (2013.01)

(58) Field of Classification Search
CPC .............. H01J 49/0036; H01J 49/0009; G01N 33/6848

(Continued)

(56) References Cited

U.S. PATENT DOCUMENTS 6,983,213 B2   1/2006   Wang
7,451,052 B2   11/2008  Wang et al.

(Continued)

FOREIGN PATENT DOCUMENTS

WO   2004050839 A2   6/2004
WO   2016196432 A1   12/2016

OTHER PUBLICATIONS

Wang, et al.; "The Concept of Spectral Accuracy for MS"; Analytical Chemistry, 2010, vol. 82, 7055-7062.

(Continued)

*Primary Examiner* — Michael Maskell
(74) *Attorney, Agent, or Firm* — Ohlandt, Greeley, Ruggiero and Perle, LLP

(57) ABSTRACT

A method for mass spectral analysis of molecules based on full mass spectral profile or raw scan mode data, comprising the steps of specifying the basic building blocks for the molecule; estimating initial values including trial numbers of building blocks, charge states, and possible modifications; calculating discrete isotope distributions based on elemental compositions; calculating a profile mode theoretical mass spectrum using a target mass spectrum peak shape function; performing regression analysis between acquired profile mode mass spectrum data and calculated theoretical mass spectrum data and reporting regression statistics; using regression statistics as feedbacks to update initially estimated values including trial numbers of building blocks, charge states, and possible modifications; and repeating selected step to optimize the regression statistics. A mass spectrometer operating in accordance with the method. A medium having computer readable program instructions for causing a mass spectrometer associated with a computer to operate in accordance with the method.

22 Claims, 6 Drawing Sheets

Related U.S. Application Data

(60) Provisional application No. 62/679,720, filed on Jun. 1, 2018.

(58) Field of Classification Search
USPC .............................. 250/281, 282; 702/27, 28
See application file for complete search history.

(56) References Cited

U.S. PATENT DOCUMENTS

| | | |
|---|---|---|
| 7,493,225 B2 | 2/2009 | Wang |
| 7,781,729 B2 | 8/2010 | Wang et al. |
| 8,803,080 B2 | 8/2014 | Wang et al. |
| 2002/0172961 A1* | 11/2002 | Schneider .......... G01N 33/6848 435/6.12 |
| 2004/0180446 A1* | 9/2004 | Thompson ......... G01N 33/6848 436/173 |
| 2008/0001079 A1* | 1/2008 | Wang .................. H01J 49/0036 250/282 |
| 2013/0095514 A1* | 4/2013 | Zerweck .................. C07K 2/00 435/23 |
| 2014/0248603 A1 | 9/2014 | Eichmeyer et al. |
| 2014/0330524 A1* | 11/2014 | Geromanos ......... H01J 49/0036 702/19 |
| 2017/0370942 A1* | 12/2017 | Picotti .................... G01N 33/58 |
| 2018/0088094 A1* | 3/2018 | Yu ...................... G01N 33/6848 |

OTHER PUBLICATIONS

Hannesh, S.M.; Electrophoresis 21, 2000, 1202-1209.

International Search Report dated Aug. 22, 2019 from corresponding International Patent Application No. PCT/US2019/035173, 3 pages.

Written Opinion dated Aug. 22, 2019 from corresponding International Patent Application No. PCT/US2019/035173, 8 pages.

Kind, et al.; "Seven Golden Rules for Heuristic Filtering of Molecular Formulas Obtained by Accorate Mass Spectrometry"; BMC Bioinformatics 2007, 8:105, Mar. 27, 2007; http://www.biomedcentral.com/1471-2105/8/105.

Mann, et al.; "Interpreting Mass Spectra of Multiply Charged Ions", Analytical Chemistry, vol. 61, No. 15, Aug. 1, 1989, 1702-1708.

* cited by examiner

MASS SPECTRAL ANALYSIS OF LARGE MOLECULES

CROSS-REFERENCE TO RELATED PATENT DOCUMENTS

This application is related to the following patent documents, which may be regarded as useful background for understanding the present application:

U.S. Pat. Nos. 6,983,213, 7,493,225, 7,577,538, 7,451,052, 7,781,729, 8,927,925, and 8,803,080.

International Patent Application PCT/US2005/039186, filed on Oct. 28, 2005.

The entire teachings of these patent documents are hereby incorporated herein by reference, in their entireties, for all purposes.

BACKGROUND OF THE DISCLOSURE

1. Field of the Disclosure

The present disclosure relates to mass spectrometers. In particular it relates to improvements and applications with respect to the teachings of the above referenced patent documents.

2. Description of the Related Art

The background art has been described in the above referenced patent documents. Specifically, for the mass spectral (MS) analysis of small molecules, whose mass or m/z (where z is likely 1 for single charge) is typically under 1,000 Da and is typically composed of C, H, N, O, P, S, Cl etc. and some metal atoms such as Na or K, its monoisotopes are quite abundant (if not the most abundant), and therefore easily observable and measured, especially with higher resolution MS instruments such as Time of Flight (TOF), Orbitrap, or FT ICR MS. The monoisotope can be so accurately measured that it has become the bedrock of elemental composition determination, as mentioned in the above referenced patents. It is typically assumed that a monoisotope mass accuracy of less than 1-5 ppm would be sufficient to attain reasonable determination of elemental composition for unknown small molecule compounds, although the inventor has published a front cover feature article (Analytical Chemistry, 2010, Vol 82, 7055-7062) pointing out that full spectral analysis involving all significant isotopes including A, A+1, A+2 etc. in the full profile mode and associated full spectral accuracy can provide far more accurate determination of elemental composition than using the single point measurement of the monoisotope mass location. The inventor disclosed that with full spectral data and associated spectral accuracy, it is even possible to determine elemental compositions using a conventional single quadrupole MS system under normal chromatographic separation and data acquisition conditions, due to the availability of additional spectral information coming from other higher isotopes. In order to take advantage of this additional spectral information involving other higher isotopes, the inventor has shown that it is necessary to perform a new type of MS calibration that involves not only the m/z ratio, but more importantly, the MS peak shape as well, which leads to a high level of spectral accuracy after this new type of MS calibration, with references made to U.S. Pat. Nos. 6,983,213 and 8,803,080.

For larger molecules found in polymer and biological applications, such as polyethylene glycol (PEG), oligos (various forms of DNA or RNA), peptides, antibodies, or proteins, the monoisotope becomes less and less abundant due to the smaller and smaller statistical probability of forming a molecule with all its atoms from the lowest possible isotope. When the monoisotope becomes weaker, it is harder to get an accurate measurement of its mass. The more abundant isotopes can still be measured accurately, even though the higher isotopes are typically composed of many closely located isobars, for example, A+1 may contain contributions from $^{13}C$, $^{15}N$, $^{2}H$, $^{33}S$ etc. whereas the A+2 may contain contributions from even more isobars such as $[^{13}C]_2$, $^{18}O$, $[^{13}C^2H]$, $[^{13}C^{15}N]$, $[^{13}C^{33}S]$, $^{34}S$ etc. The accurate mass measurement of such a composite isotope peak as A+1, A+2 etc. becomes difficult, if not impossible, without a properly defined MS peak shape function, available after the afore-mentioned full mass spectral calibration. However, due to the presence and contributions of other closely located isobars, such a measurement of a single accurate mass location on higher isotopes would remain questionable and highly undesirable, if not outright meaningless, due to the reduction of viable degrees of freedom from multiple independent variables at A+1 and A+2 down to a single number. FIG. 2 shows a trypsin-digested peptide mass spectrum measured on a LC Orbitrap MS system with charge z=2 where the monoisotope is no longer the most abundant, and FIG. 3 shows a 20-mer oligo measured on a LC/TOF MS system with charge z=-4 where the monoisotope is further diminished.

Compounding the above difficulties, challenges, uncertainties and ambiguities, is the issue of multiple charges, a phenomenon typical of electrospray ionization available in nearly all LC/MS systems, where multiple charges can be placed on an otherwise neutral molecule during the ionization process, allowing for a large molecule to be measured at a significantly smaller m/z range more accessible on a broad range of conventional MS systems. For example, a 25 KDa biomolecule may be observed at m/z 2,500 with a charge z=10. While convenient, this makes the mass spectrum 10 times more compact in terms of active m/z range (x-axis) where there are observable mass spectral intensities, i.e., the ~1 Da separation between A and A+1 is now reduced by 10 times, or shrunk to 0.1 Da, making the spectral separation between them 10 times smaller, and accurate mass determination of the monoisotopic peak (A) or A+1 more difficult. As the molecule gets larger and larger, its monoisotope becomes less and less abundant, its charge state becomes higher and higher leading to further compression of the mass spectral isotope cluster spacings, while the typical MS spectral resolution becomes worse and worse (mass spectral peak width such as FWHM becomes wider and wider). The monoisotope peak can disappear completely and become unobservable for practical purposes. This happens even with the most expensive high-end MS instrumentation for monoclonal antibodies (mAb) or large proteins such as bovine serum albumin (BSA), but occurs for much smaller molecules such as 40-mer oligos on a unit mass resolution quadrupole MS system. FIG. 4 shows BSA with a ligand on a MALDI MS TOF system specially fitted with high mass detector and FIG. 5 shows the same 20-mer oligo as that from FIG. 3 but measured on a LC single quadrupole MS with charge z=-3. In both cases, the isotopes clusters become so overlapped with each other that there are neither observable spectral separation among the more abundant isotope clusters nor observable monoisotopic peak.

With the multiply charged ions created from ESI, the conventional data processing approaches were based on the original publication by Mann, Meng and Fenn from Analytical Chemistry, 1989, Vol 61 (15), 1702-1708, to first determine the charge state z by analyzing the m/z gaps between adjacent isotope clusters (1/z) and/or adjacent charge states, and then reconstruct what a singly charged mass spectrum would have looked like, either in the centroid mode in early days or in profile mode more recently, without requiring the exact knowledge of the MS peak shape function or elemental composition which gives rise to the measured isotope clusters with varying charge states. While working reasonably well for small enough molecules (thus smaller charge states) with enough spectral resolution and signal to noise, this approach can lead to grossly wrong estimates for the charge states and complete mis-identification of the molecular (average) mass, and more significantly to a mistake in the exact determination of the underlying molecule which gives rise to the mass spectral response. For the ever-increasing size of the biomolecules being analyzed, the ever-decreasing quantity of the materials being measured, and the presence of other interfering ions or modifications and associated charge states and charge state distributions, which is beyond what this method was originally designed and intended for, erroneous results without much available warnings have been observed, reported, or even published, unfortunately, in many modern MS laboratories.

It should be noted that even for small molecules with masses at less than 1000 Da, the monoisotope may also be weak or even unobservable; for example, for metalorganic compounds containing Li, B, Hg, Sn, or other elements whose elemental monoisotope is not the most abundant or too weak relative to the other higher isotopes. Furthermore, even for molecules whose monistope is both baseline resolved and the most abundant, there have been many cases where the elemental composition search within a given mass error window of, 1-5 ppm, for example, from the determined accurate mass just happens to leave the correct elemental composition out, due to either overly optimistic mass error settings (aggressively small) or simply random statistical fluctuations, to which a single point accurate mass measurement of the monoisotopic peak is more susceptible. Just as an example, the correct elemental composition that has an actual mass error of 5.1 ppm when the mass error window is optimistically set at 5.0 ppm would be completely missed during the search of possible elemental compositions and never even considered as a possibility, leading to incorrect and possibly costly mis-identifications. On the other hand, a more generous mass error setting of 10-15 ppm would include too many possible elemental composition candidates (with the correct elemental composition among them) would not be practically useful and helpful to the end users. Computationally, all existing approaches for small molecule elemental composition determination revolves around evaluating all possible elemental compositions whose exact monoisotopic mass falls within a given mass tolerance window, regardless of how spectrally unfeasible some of the elemental compositions are. This is a rather inefficient computation process, especially at higher m/z values >800-1000 for true unknown identification, where 1 ppm mass tolerance may involve hundreds, if not thousands or tens of thousands, possibilities.

Another difficulty of currently available analysis methods is the interference from co-existing and mutually interfering ions. The spectral contribution from the interfering ions can potentially alter the accurate mass measurement of the monoisotopic peak, if and when interfered with, but also the overall mass spectral response across the entire isotope cluster or profile, leading to incorrect results without any warning and with possibly costly consequences. For small molecules, this may arise from the EI fragmentation where (M-H)+ would interfere with M+ for quadruple GC/MS analysis. For large molecules, as one of many possible biologics modifications, the deamidation or deamination would result in only ~1/z change in the overall m/z when compared to the original native form of the biologics, creating a spectral interference difficult or impossible to separate either mass spectrally or chromatographically, even with high resolution MS instrumentation or elaborate HPLC separation running a long gradients. To make the matter worse, these mutually interfering ions may even have different charge states, especially in DNA or RNA sequencing applications, further complicating the attempt at accurate and unbiased analysis.

A new approach to analyze large or small molecules is desired, which can take advantage of the full spectral responses dominated by any arbitrary number of isotopes, but also include the weaker isotopes, regardless of whether the most abundant isotope happens to be the monoisotope, with or without the mass spectral resolution capable of spectrally separating the isotope clusters, with any possible charge state/distribution, and with or without co-existing and mutual interfering possible mixture components.

It is the objective of this disclosure to overcome the above-mentioned shortcomings and difficulties of existing methods and to provide a new mass spectral analysis approach.

SUMMARY OF THE DISCLOSURE

The present application is directed to the following improvements:

1. An accurate approach for the determination of small or large molecules in terms of their basic building blocks (or repeating units): elemental compositions (C, H, N, O, S, P or other elements from the periodic table) for small molecules; repeating units for polymers; A, G, T, C for oligos; A, U, G, C for RNA; amino acids for peptides or proteins and possible associated modifications, all based on full spectral analysis accounting for or fitting to the actual measured profile mode mass spectral data by including possibly all significant isotopes and using spectral accuracy or spectral fitting residual as the objective function in a constrained nonlinear optimization process. It is advantageous to use spectrally calibrated MS profile mode data, instead of either the centroid data or profile mode data with m/z-only calibration currently in wide use. Reference is made to U.S. Pat. Nos. 6,983,213, 7,493,225, and 8,803,080.

2. Constraints can be added to make the process computationally more efficient.

3. Chemical or biological modifications can be incorporated to allow for mixture mode analysis, with or without mass spectral or chromatographic separation.

4. The process can be applied to successive LC retention time windows containing successive sequence ladders for de novo sequencing applications.

5. This process can be applied to successive m/z range windows containing successive sequence of MS fragments for de novo sequencing applications.

6. This process can be applied to samples containing multiple original molecules in a multiplex mode to increase the throughput of the analysis.

Each of these aspects will be described below to demonstrate their utilities.

In general, this disclosure is directed to a method for mass spectral analysis of molecules based on full mass spectral profile or raw scan mode data, comprising the steps of specifying the basic building blocks for the molecule; estimating initial values including trial numbers of building blocks, charge states, and possible modifications; calculating discrete isotope distributions based on elemental compositions; calculating a profile mode theoretical mass spectrum using a target mass spectrum peak shape function; performing regression analysis between acquired profile mode mass spectrum data and calculated theoretical mass spectrum data and reporting regression statistics; using regression statistics as feedbacks to update initially estimated values including trial numbers of building blocks, charge states, and possible modifications; and repeating selected step to optimize the regression statistics.

The disclosure is also directed to a mass spectrometer operating in accordance with the method.

The disclosure is further directed to computer readable medium having computer readable program instructions for causing a mass spectrometer associated with a computer to operate in accordance with the method.

BRIEF DESCRIPTION OF THE DRAWINGS

A component or a feature that is common to more than one drawing is indicated with the same reference number in each of the drawings.

DESCRIPTION OF THE EMBODIMENTS

Figure 1:
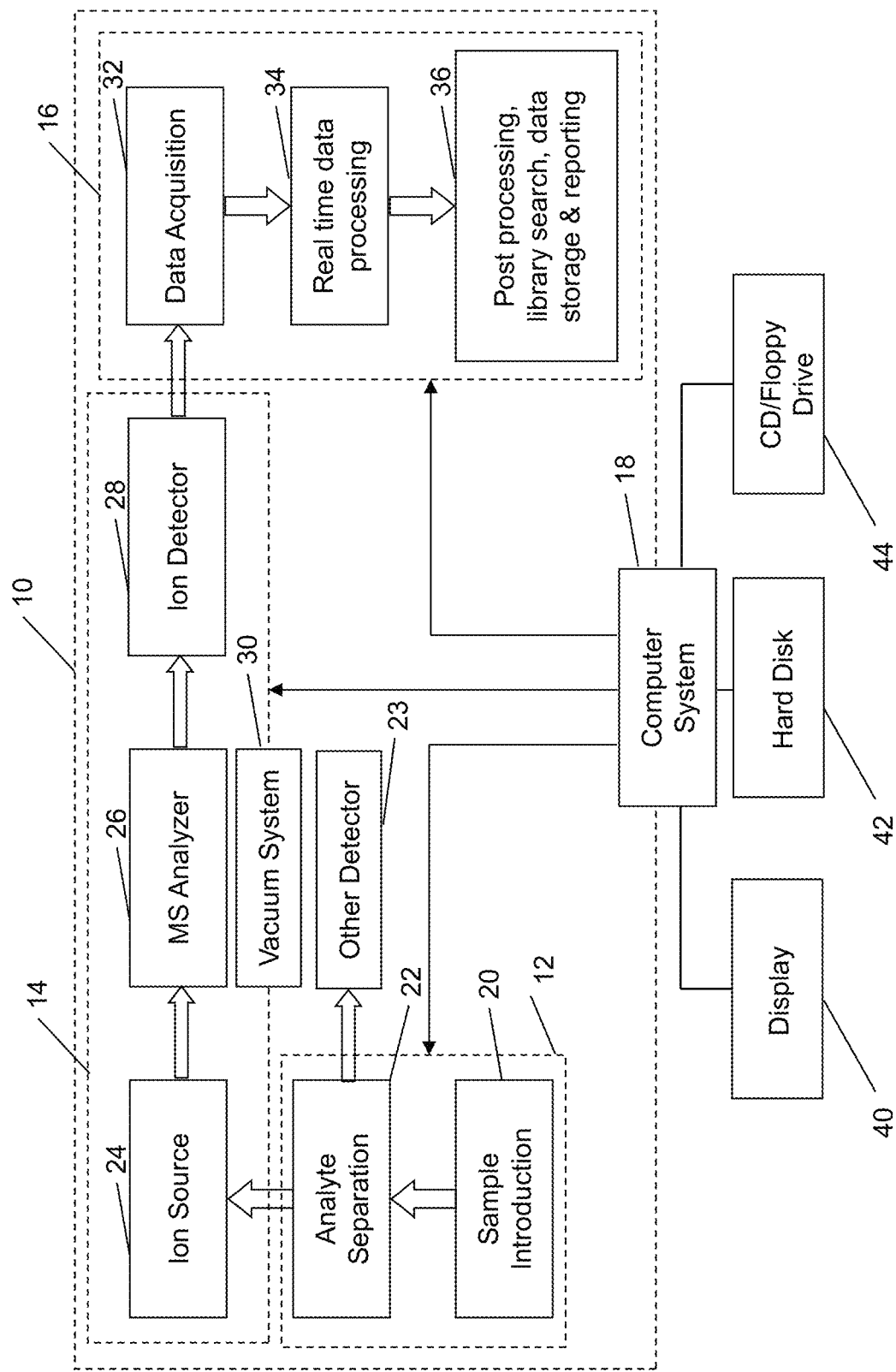
FIG. 1 is a block diagram of a mass spectrometer system that can utilize the methods disclosed herein.
Figure 2:
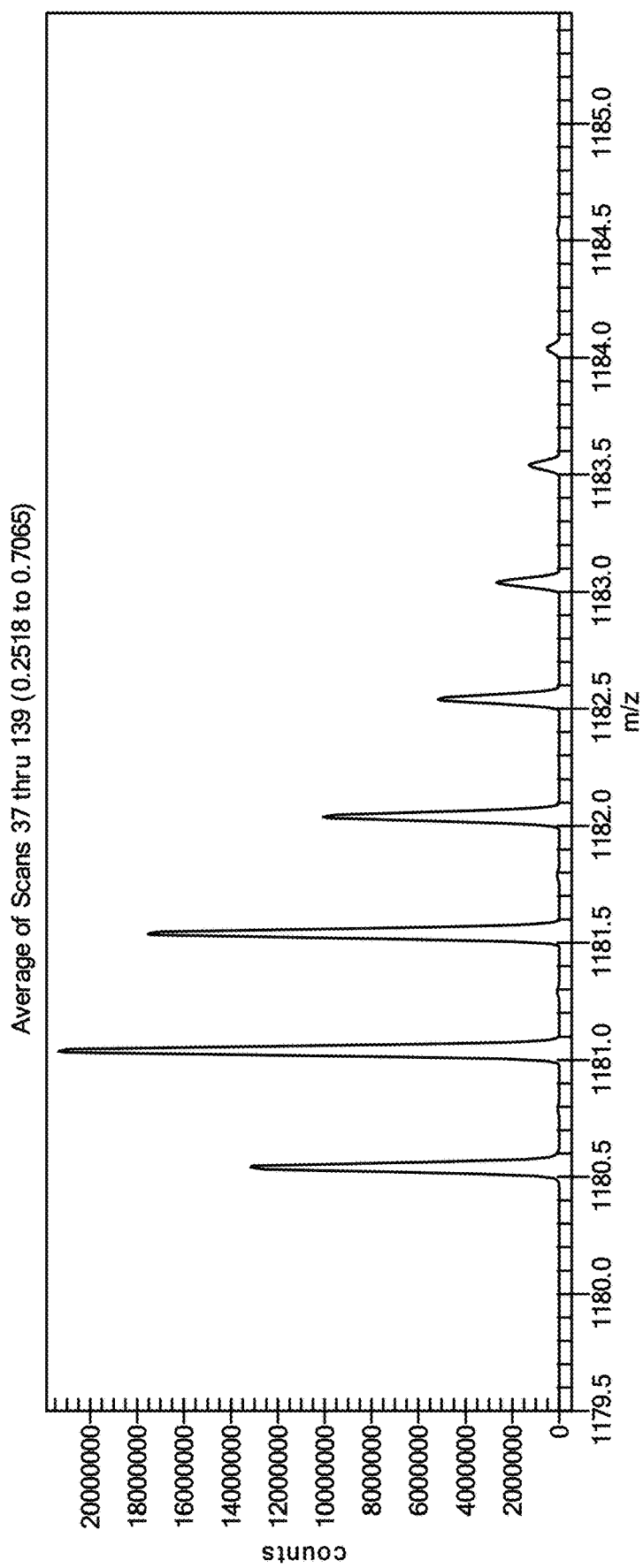
FIG. 2 show a peptide with z=2 charges measured with LC Orbitrap MS.
Figure 3:
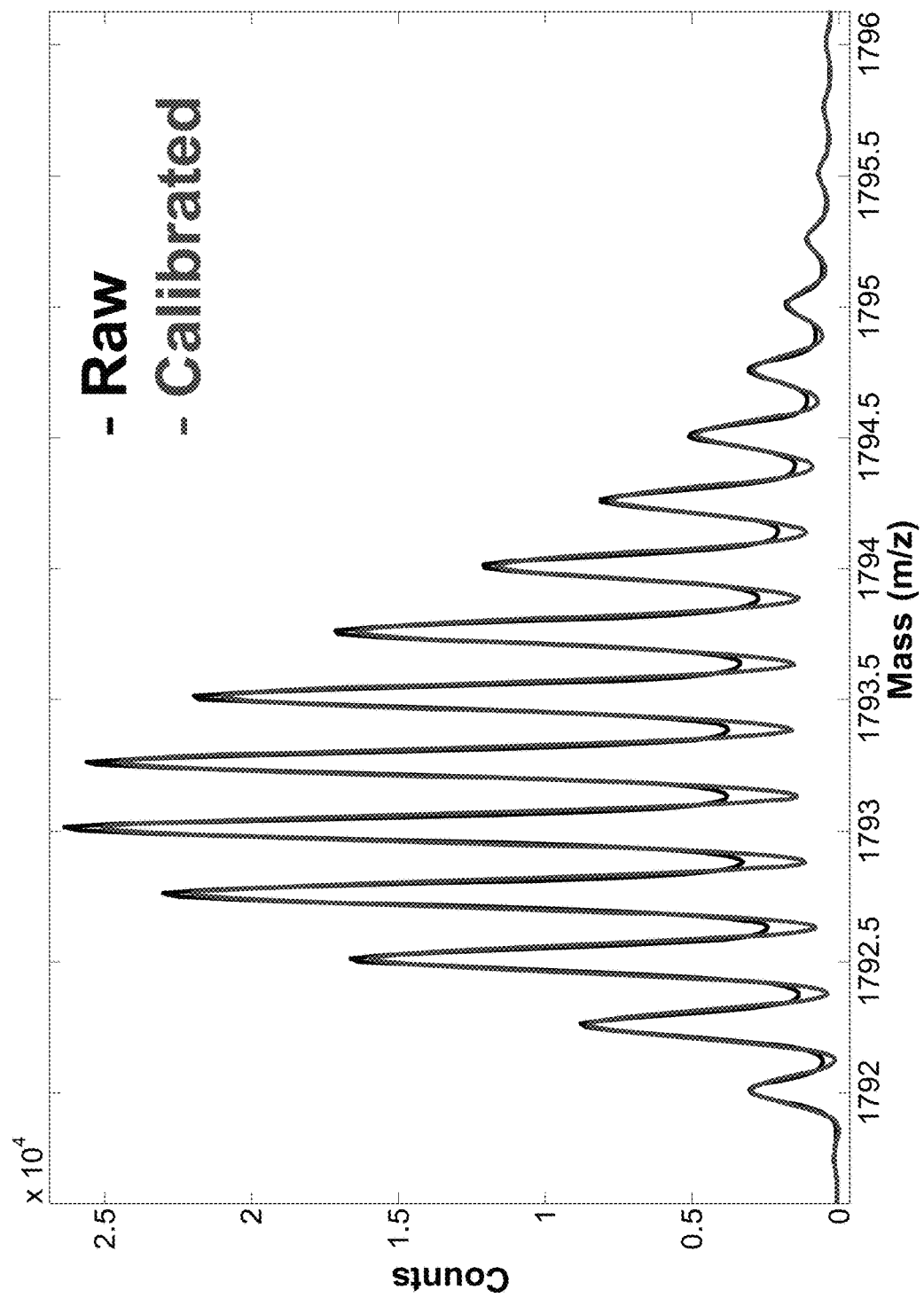
FIG. 3 shows a 20-mer oligo measured on LC TOF MS with z=−4 charges.
Figure 4:
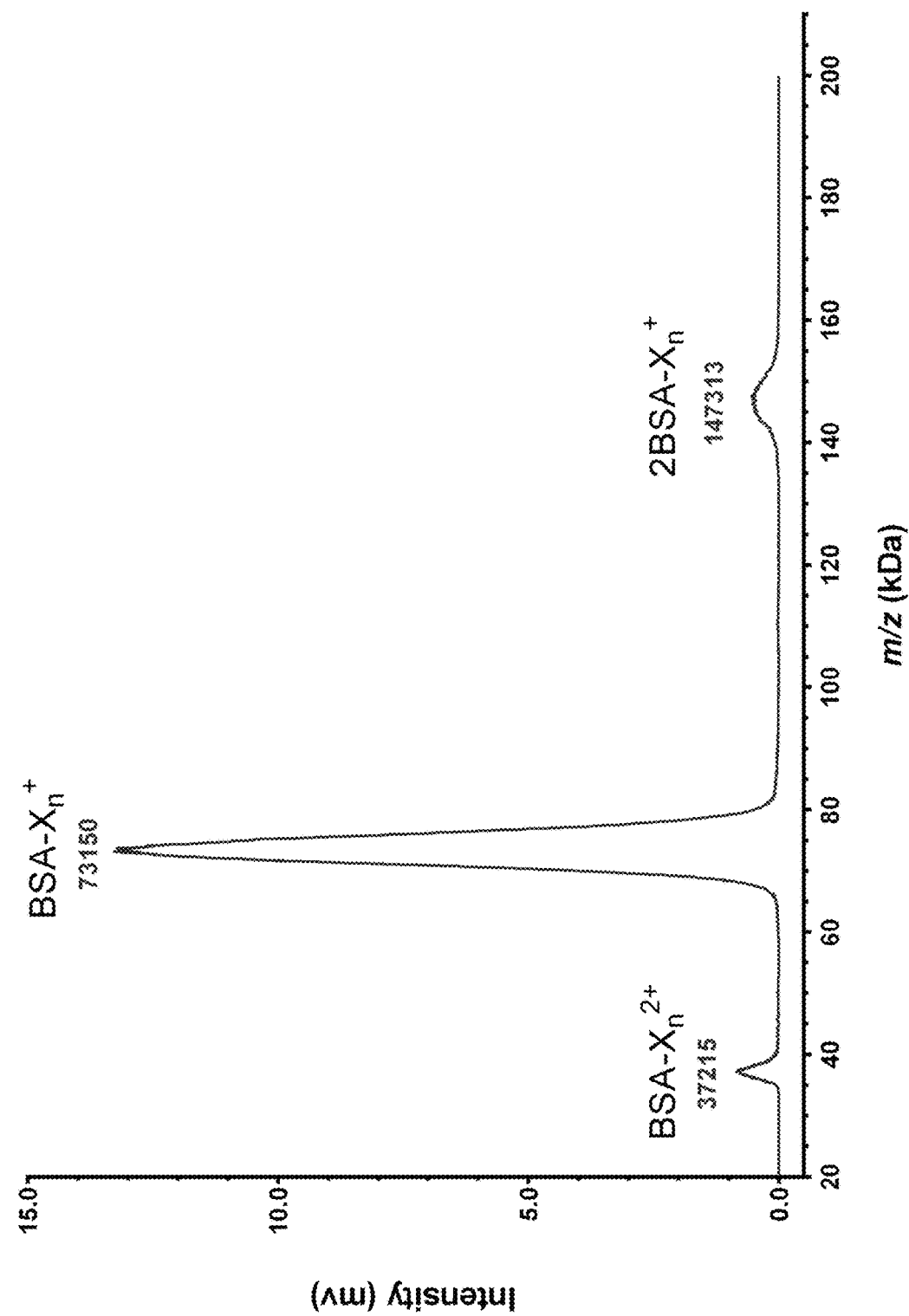
FIG. 4 shows a BSA-ligand measured on MALDI TOF with high mass detector fitted.
Figure 5:
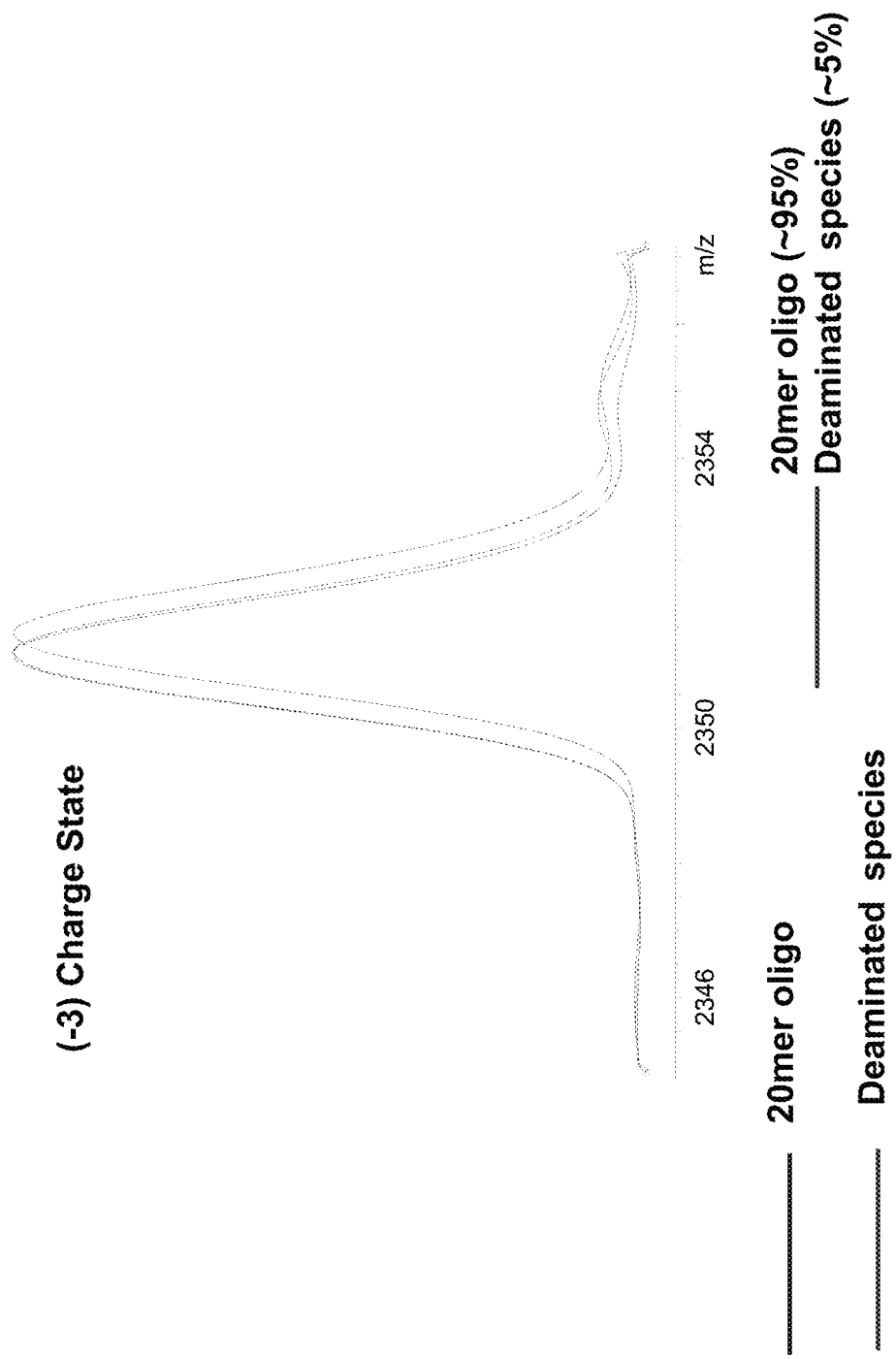
FIG. 5 shows a 20-mer oligo measured on LC single quadrupole MS with z=−3 charges.

FIG. 1 is a block diagram of a mass spectrometer system that can utilize the methods disclosed herein.

Referring to FIG. 1, there is shown a block diagram of an analysis system 10, that may be used to analyze proteins or other molecules, as noted above, incorporating features of the present disclosure. Although the present disclosure will be described with reference to the single embodiment shown in the drawings, it should be understood that it can be embodied in many alternate forms of embodiments. In addition, any suitable types of components could be used.

Analysis system 10 has a sample preparation portion 12, other detector portion 23, a mass spectrometer portion 14, a data analysis system 16, and a computer system 18. The sample preparation portion 12 may include a sample introduction unit 20, of the type that introduces a sample containing proteins, peptides, or small molecule drug of interest to system 10, such as an LCQ Deca XP Max, manufactured by Thermo Fisher Scientific Corporation of Waltham, Mass., USA. The sample preparation portion 12 may also include an analyte separation unit 22, which is used to perform a preliminary separation of analytes, such as the proteins to be analyzed by system 10. Analyte separation unit 22 may be any one of a chromatography column, an electrophoresis separation unit, such as a gel-based separation unit manufactured by Bio-Rad Laboratories, Inc. of Hercules, Calif., or other separation apparatus such as ion mobility or pyrolysis, etc. as is well known in the art. In electrophoresis, a voltage is applied to the unit to cause the proteins to be separated as a function of one or more variables, such as migration speed through a capillary tube, isoelectric focusing point (Hannesh, S. M., Electrophoresis 21, 1202-1209 (2000), or by mass (one dimensional separation)) or by more than one of these variables such as by isoelectric focusing and by mass. An example of the latter is known as two-dimensional electrophoresis.

The mass spectrometer portion 14 may be a conventional mass spectrometer and may be any one available, but is preferably one of TOF, quadrupole MS, ion trap MS, qTOF, TOF/TOF, or FTMS. If it has an electrospray ionization (ESI) ion source, such ion source may also provide for sample input to the mass spectrometer portion 14. In general, mass spectrometer portion 14 may include an ion source 24, a mass analyzer 26 for separating ions generated by ion source 24 by mass to charge ratio, an ion detector portion 28 for detecting the ions from mass analyzer 26, and a vacuum system 30 for maintaining a sufficient vacuum for mass spectrometer portion 14 to operate most effectively. If mass spectrometer portion 14 is an ion mobility spectrometer, generally no vacuum system is needed and the data generated are typically called a plasmagram instead of a mass spectrum.

In parallel to the mass spectrometer portion 14, there may be other detector portion 23, where a portion of the flow is diverted to, for nearly parallel detection of the sample in a split flow arrangement. This other detector portion 23 may be a single channel UV detector, a multi-channel UV spectrometer, or Reflective Index (RI) detector, light scattering detector, radioactivity monitor (RAM) etc. RAM is most widely used in drug metabolism research for Carbon 14 14C-labeled experiments where the various metabolites can be traced in near real time and correlated to the mass spectral scans.

The data analysis system 16 includes a data acquisition portion 32, which may include one or a series of analog to digital converters (not shown) for converting signals from ion detector portion 28 into digital data. This digital data is provided to a real time data processing portion 34, which processes the digital data through operations such as summing and/or averaging. A post processing portion 36 may be used to do additional processing of the data from real time data processing portion 34, including library searches, data storage and data reporting.

Computer system 18 provides control of sample preparation portion 12, mass spectrometer portion 14, other detector portion 23, and data analysis system 16, in the manner described below. Computer system 18 may have a conventional computer monitor or display 40 to allow for the entry of data on appropriate screen displays, for example, with a keyboard (not shown), and for the display of the results of the analyses performed. Computer system 18 may be based on any appropriate personal computer, operating for example with a Windows® or UNIX® operating system, or any other appropriate operating system. Computer system 18 will typically have a hard drive 42 or other type of data storage medium, on which the operating system and the program for performing the data analysis described below, is stored. A removable data storage device 44 for accepting a CD, floppy disk, memory stick or other data storage medium is used to load the program in accordance with the invention on to computer system 18. The program for controlling sample preparation portion 12 and mass spectrometer portion 14 will typically be downloaded as firmware for these portions of system 10. Data analysis system 16 may be a program written to implement the processing steps discussed below, in any of several programming languages such as C++, JAVA or Visual Basic.

In the preferred embodiment, a sample containing one or more molecules is acquired through the chromatography/mass spectrometry system described in FIG. 1 with mass spectral profile mode (raw scan data) continuously acquired throughout the run. Standard molecules of known elemental compositions can be acquired either internally or externally to perform the mass accuracy and spectral accuracy calibration to the raw profile mode mass spectral data before subsequent processing and analysis, using the approach described in the U.S. Pat. No. 6,983,213. Step 51 in FIG. 6 corresponds to the profile mode data acquisition and MS calibration to convert mass spectral peak shape into a known target peak shape function for later use. Without this peak shape calibration, one may have to resort to estimated peak shape function, assumed peak shape function, or a measured peak shape function at another m/z or time or under a different MS condition, resulting in sub-optimal results.

Figure 6:
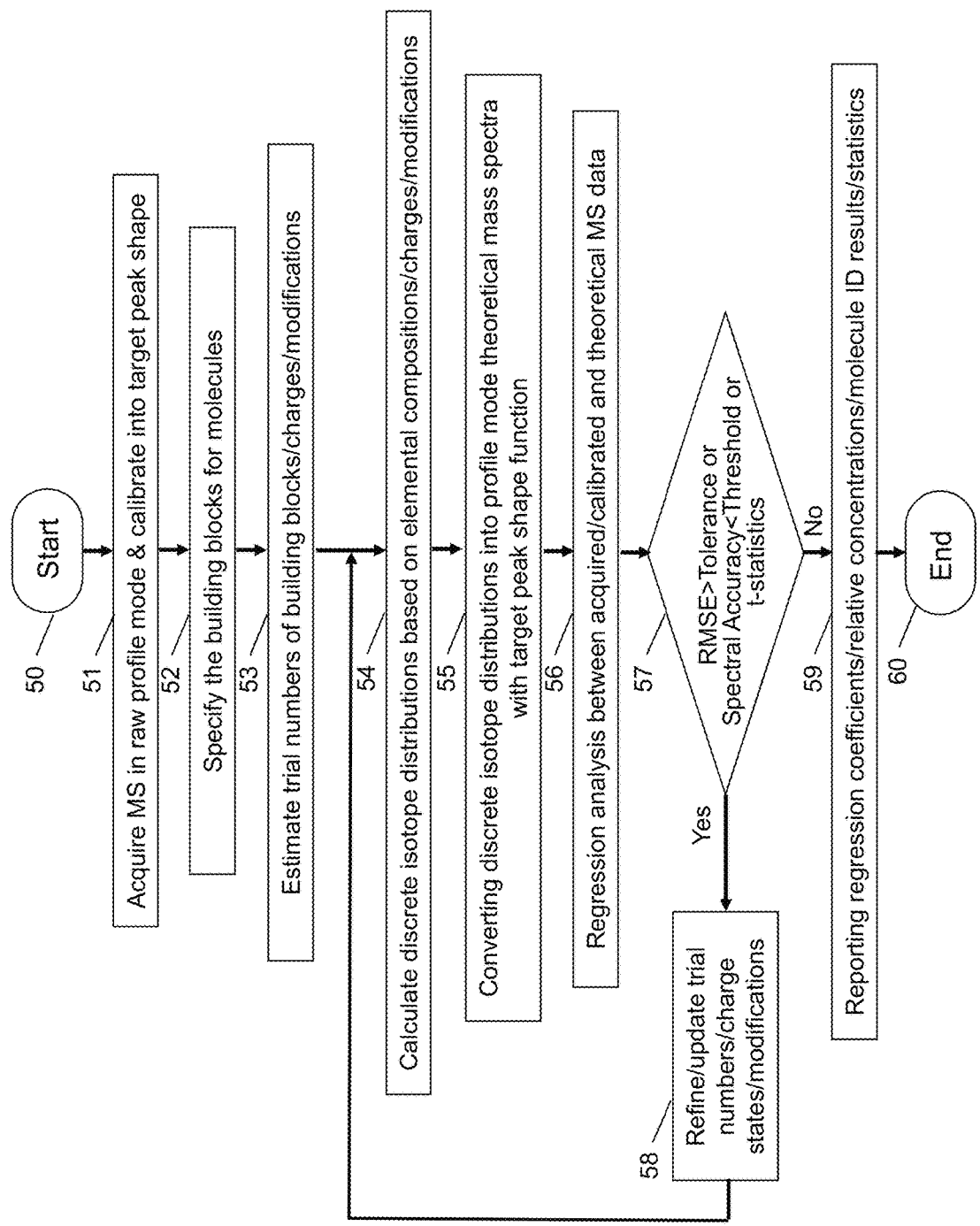
FIG. 6 is a flow chart of an embodiment disclosed herein.

The detailed steps involved in the subsequent processing and analysis would now be described:

1. Referring to FIG. 6 there is depicted, starting at step 50, the new method for the determination of small or large molecules in terms of their basic building blocks: elemental compositions (C, H, N, O, S, P, or any other elements from the periodic table) for small molecules; repeating units for polymers; A, G, T, C for oligos; A, U, G, C for RNA; amino acids for peptides or proteins and possible associated modifications, all based on full spectral analysis accounting for or fitting to the actual measured profile mode mass spectral data by including possibly all significant isotopes and using spectral accuracy or spectral fitting residual as the objective function in a constrained or non-constrained, linear or non-linear optimization process. At step 52, it is advantageous to use spectrally calibrated MS profile mode data, instead of either the centroid data or profile mode data with m/z-only calibration currently in wide use. Reference is made to U.S. Pat. Nos. 6,983,213, 7,493,225, and 8,803,080.

2. The constrained nonlinear optimization process may take the form of a linear or nonlinear (integer) programming for the determination of the number of each possible building block that comprise the molecule, i.e., determination of a, b, c, d, e, . . . from the given molecular representation $AaBbCcDdEe$ . . . , where A, B, C, D, E are the building blocks and a, b, c, d, e . . . are the integer numbers of corresponding building blocks contained in the molecule, for example, the oligo sequence of AGTCCCGA would be represented as $A_2G_2T_1C_3$. Step 53 depicts the start of this optimization process by initially estimating a set of trial values for the number of building blocks, charge states, and possible modifications.

3. For each set of possible a, b, c, d, e, . . . and based on the elemental compositions of each building blocks A, B, C, D, E, . . . , the combined elemental composition is known and its corresponding theoretical discrete isotope distribution can be calculated for each given charge state (Step 54) before convoluting or combining with the same target MS peak shape function into which the actually measured MS has been calibrated to form a profile mode theoretical mass spectrum (Step 55). A spectral fitting or regression analysis between the theoretical (possibly many including different charges and modifications, additional species, or combinations thereof) and the calibrated MS can be performed (Step 56) to arrive at a fitting spectral residual (RMSE or Root Mean Squared Error), Spectral Accuracy (SA), t-value or t-statistics.

4. The objective is to find a set of a, b, c, d, e, . . . that maximizes Spectral Accuracy (SA) or minimizes Spectral Residual (RMSE) or other statistics such as t-value or t-statistics (Step 57). This can be accomplished through various optimization algorithms including Simplex, integer programming, linear or nonlinear programming, or appropriate modifications or adaptions. These exact optimization algorithms can be applied to improve or update the initial trial values (Step 58) for the next iteration until convergence at Step 57, when the RMSE error is at or below the random noise in the actual MS data, the corresponding spectral accuracy is at or above the expected signal to noise, or the t-values of the estimated parameters all are statistically significant, or some combination thereof.

5. Spectral contributions from interference ions including possible modifications (including possible impurities, degradants, or biotransformation products such as deamidation, deamination, oxidation, di-sulfide bond formation or sodium or potassium adducts) can be accommodated in the spectral fitting process (under mixture mode, with reference made to U.S. Pat. Nos. 7,451,052 and 7,781,729) to arrive at their respective numbers of each of the possible building blocks that comprise the spectral interferences. The relative concentrations of various modifications, proportional or related to the fitting or regression coefficients, will also be obtained in the same fitting or regression process, which may be of great importance in either therapeutic research and development or product quality assurance or control.

6. The charge state, or the range or distribution of charge states, can also be added, as additional parameters to be determined from the above nonlinear optimization process. The charge state of one ion can be different from that of an interference ion. The charge states or their distribution can follow a prescribed or imposed functional form or each charge state can be treated independently as a separate ion, with its corresponding discrete isotope distribution calculated for a specific or distribution of charge state(s) and the profile mode theoretical mass spectrum/spectra formed by convoluting or combining with the same MS target peak shape function into which the actually measured MS has been calibrated. The relative concentrations for a given molecule across various charge states or a distribution can be summed together to reflect the total amount of a given molecule being measured from the sample. The total amount of a given molecule can be compared or ratioed against other molecules for relative quantitation, e.g., for example, for the determination of the percentage deamidation for a given peptide after a certain number of months in storage for shelf-life study of biotherapeutics. When the total relative amount of a given molecule is calibrated against a set of concentration standards, absolute quantitation can be achieved through standard calibration curves. This is depicted in Step 59 in the flow chart of FIG. 6.

7. Useful constraints may be added to make the computation more efficient, including the total estimated length of a particular polymer or sequence, i.e., the sum of the numbers of all building blocks equal to 50; a+b+c+d+e . . . =50, for a 50-mer or to specify it between 49-51 based on LC retention time which is known to be correlated with the length of a general sequence, through either experience or a deliberate LC calibration process using known sequence lengths. For the elemental composition determination, lower and upper boundary for the number of C, H, N, O, S, P, F, Cl etc. and other constraints such as C/H ratio etc. can be imposed, based on empirical rules of known chemical compound libraries (Tobias Kind and Oliver Fiehn, Seven golden rules for heuristic filtering of molecular formulas obtained by accurate mass spectrometry, BMC Bioinformatics, 2007, 8:105).

8. Other useful constraints include a lower boundary and/or a higher boundary for the total number of building blocks (sequence length) based on the average measured m/z range of the MS signal, for a given possible charge state z, and the possible average mass or the mass range of each possible building block.

9. When applied to mass spectral data taken from successive LC retention time windows containing successive sequence ladders, the difference in the number of building blocks calculated indicates the presence or absence of a particular building block in adjacent retention time windows, enabling the readout of one molecular sequence at a time when analyzed across a wide LC run and thus the sequencing of RNA, DNA, peptide, protein or other polymers. In this case, there is strong correlation between successive LC retention time windows in terms of the number of building blocks, e.g., the number of A, G, T, C would likely only change by +/−1 or +/−2, depending on the degree of LC separation involved, which can be used as additional constraints to speed up the computation. This can also be used to speed up the discrete isotope distribution calculation in Step 54 in FIG. 6, by updating the already available distribution calculated for a shorter sequence or smaller molecule through the addition of a few more new building blocks, rather than starting from scratch every time.

10. When applied to a mixture of sequences, this approach will enable the high throughput sequencing of more than one molecular species at a time due to the resulting multiplex advantages.

11. When applied to MS fragments containing successive sequence ladders, the difference in the number of building blocks calculated indicates the presence or absence of a particular building block in adjacent m/z mass windows, enabling the readout of one molecular sequence at a time when analyzed across a wide m/z range.

The principles disclosed herein can be applied to peptides, RNA, DNA, protein, mAb, Oligos, polymers—and their mixtures, or their MS/MS or CID or IRD fragments. Although the description above contains many specifics, these should not be construed as limiting the scope of the invention but as merely providing illustrations of some feasible embodiments of this invention.

Thus the scope of the disclosure should be determined by the appended claims and their legal equivalents, rather than by the examples given. Although the present disclosure has been described with reference to the embodiments described, it should be understood that it can be embodied in many alternate forms of embodiments. In addition, any suitable size, shape or type of elements or materials could be used. Accordingly, the present description is intended to embrace all such alternatives, modifications and variances which fall within the scope of the appended claims.

It will be understood that the disclosure may be embodied in a computer readable non-transitory storage medium storing instructions of a computer program which when executed by a computer system results in performance of steps of the method described herein. Such storage media may include any now known or developed in the future, or any of those mentioned in the description above.

The techniques described herein are exemplary, and should not be construed as implying any particular limitation on the present disclosure. It should be understood that various alternatives, combinations and modifications could be devised by those skilled in the art. For example, steps associated with the processes described herein can be performed in any order, unless otherwise specified or dictated by the steps themselves. The present disclosure is intended to embrace all such alternatives, modifications and variances that fall within the scope of the appended claims.

The terms "comprises" or "comprising" are to be interpreted as specifying the presence of the stated features, integers, steps or components, but not precluding the presence of one or more other features, integers, steps or components or groups thereof

What is claimed is:

1. A method for mass spectral analysis of ions having a minimum of two different charges based on full mass spectral profile or raw scan mode data, comprising the steps of:
   a. specifying the basic building blocks for a given molecule;
   b. estimating initial values including trial integer numbers of building blocks and charge states, and considering possible modifications;
   c. calculating discrete isotope distributions based on elemental compositions for each charge state;
   d. calculating a profile mode theoretical mass spectrum using a target mass spectrum peak shape function;
   e. performing regression analysis between acquired profile mode mass spectrum data and calculated theoretical mass spectrum data and reporting regression statistics;
   f. using regression statistics as feedbacks to update initially estimated values including trial integer numbers of building blocks and charge states, and possible modifications;
   g. repeating step c, d, e, and f to optimize the regression statistics; and
   h. summing relative concentrations of the ions having different charge states to determine the total concentration of the given molecule.

2. The method of claim 1, where the acquired profile mode mass spectral data is calibrated to have a given and known target peak shape.

3. The method of claim 1, where the molecule is DNA and the building blocks are the known DNA bases.

4. The method of claim 1, where the molecule is RNA and the building blocks are the corresponding nucleotides.

5. The method of claim 1, where the molecule is a peptide and the building blocks are the corresponding amino acids.

6. The method of claim 1, where the molecule is an oligonucleotide and the building blocks are the corresponding nucleotides.

7. The method of claim 1, where the molecule is a polymer and the building blocks are the basic repeating chemical units.

8. The method of claim 1, where the molecule is a small molecule chemical compound and the building blocks are the basic chemical elements taken from the periodic table, including one of C, H, N, O for organic compounds.

9. The method of claim 1, where the target mass spectrum peak shape is one of actually measured mass spectrum peak shape, estimated peak shape, and calibrated peak shape.

10. The method of claim 1, where the regression statistics includes one of root mean squared error (RMSE), spectral accuracy, and t-statistics for any of the estimated regression coefficients.

11. The method of claim 1, where updating the initial estimated values including trial numbers of building blocks, charge states, and possible modifications is carried out as part of an optimization scheme including at least one of linear optimization, nonlinear optimization, simplex optimization, integer programming, linear and nonlinear programming.

12. The method of claim 1, where the molecule to be analyzed is already known and the analysis is a confirmation including no additional iteration or updating.

13. The method of claim 1, where regression coefficients associated with one of a molecule and a modification, with a given charge state, reflect a relative amounts of the molecule and the modification.

14. The method of claim 13, where all relative amounts associated with at least one of the molecule and the modification and both are combined across all charge states and compared with each other for relative quantitation of at least one of molecules, impurities, degradants, or other biotransformation products.

15. The method of claim 13, where all relative amounts associated with at least one of the molecule and the modification and both are combined across all charge states and calibrated with those from a known concentration standard or standard series, for absolute quantitation of at least one of molecules, impurities, degradants, or other biotransformation products.

16. The method of claim 13, where the modification is one of deamidation or deamination.

17. The method of claim 14, where the biotransformation is one of deamidation or deamination and its relative quantitation is performed for one of stability study and quality control of biotherapeutics.

18. The method of claim 1, where acquired mass spectral data is derived from successive retention time windows during a chromatographic separation and the molecules under analysis correspond to chemical ladders or fragments created for sequencing of one of DNA, RNA, oligonucleotides, peptides, and proteins.

19. The method of claim 1, where acquired mass spectral data is derived from successive m/z windows within a mass spectrum and the molecules under analysis correspond to chemical ladders or fragments created for sequencing of one of DNA, RNA, oligonucleotides, peptides, and proteins.

20. The method of claim 1, where one of upper boundaries, lower boundaries, mathematical, and statistical functional forms can be imposed on the possible trial values to speed up the computational process.

21. A mass spectrometer operating in accordance with the method of claim 1.

22. For use with a computer associated with a mass spectrometer, a computer readable medium having computer readable program instructions readable by the computer for causing the mass spectrometer to operate in accordance with the method of claim 1.

* * * * *